(12) United States Patent
Tromble

(10) Patent No.: US 6,275,998 B1
(45) Date of Patent: Aug. 21, 2001

(54) VISION OCCLUDING EYE SHIELD FOR VEHICLE PASSENGERS

(76) Inventor: David Tromble, 1292 Creek Bend Rd., Jacksonville, FL (US) 32259

( * ) Notice: Subject to any disclaimer, the term of this patent is extended or adjusted under 35 U.S.C. 154(b) by 0 days.

(21) Appl. No.: 09/376,751

(22) Filed: Aug. 17, 1999

(51) Int. Cl.[7] ....................................................... A61F 9/02
(52) U.S. Cl. .......................... 2/449; 2/15; 351/45; 600/27
(58) Field of Search .................... 2/12, 13, 9, 15, 2/10, 11, 6.3, 6.7, 426, 427, 431, 433, 447, 449, 450, 454, 6.1, 410; 128/857, 858; 351/45, 46, 165, 41; 600/27

(56) References Cited

U.S. PATENT DOCUMENTS

| | | | |
|---|---|---|---|
| 2,537,768 | * | 1/1951 | LaPorte ...................................... 2/426 |
| 2,946,133 | * | 7/1960 | Williams ................................... 2/426 |
| 3,330,051 | * | 7/1967 | Pambello .................................... 2/12 |
| 3,577,566 | | 5/1971 | Kislin . |
| 3,629,870 | * | 12/1971 | Paisley ......................................... 2/15 |
| 4,106,119 | | 8/1978 | Taupin . |
| 4,411,263 | * | 10/1983 | Cook ..................................... 128/132 |
| 4,470,673 | | 9/1984 | Gilson et al. . |
| 4,644,588 | * | 2/1987 | Zawacki ...................................... 2/10 |
| 4,698,022 | * | 10/1987 | Gilson .................................... 434/36 |
| 4,859,047 | | 8/1989 | Badewitz . |
| 5,100,224 | | 3/1992 | Terrasi . |
| 5,570,144 | * | 10/1996 | Lofgren-Nisser ..................... 351/247 |
| 5,647,835 | * | 7/1997 | Martineau ............................... 600/27 |
| 5,661,534 | | 8/1997 | Gill . |
| 5,715,030 | * | 2/1998 | Quaresima ............................. 351/44 |

* cited by examiner

*Primary Examiner*—John J. Calvert
*Assistant Examiner*—Katherine Moran
(74) *Attorney, Agent, or Firm*—Thomas C. Saitta

(57) ABSTRACT

A vision occluding eye shield which completely blocks the peripheral vision of the wearer to the discernment of motion and which blocks most or all of the superior field of vision of the wearer, and preferably also blocks an upper portion of the inferior field of vision of the wearer, to the discernment of motion. When worn by a vehicle passenger the device prevents car sickness by blocking perception of objects passing through the peripheral field of vision in the side windows and through the front window, while allowing the wearer to focus on tasks or objects within the vehicle by looking through the unoccluded portion, or to look out the vehicle windows by slightly tilting the head back.

20 Claims, 3 Drawing Sheets

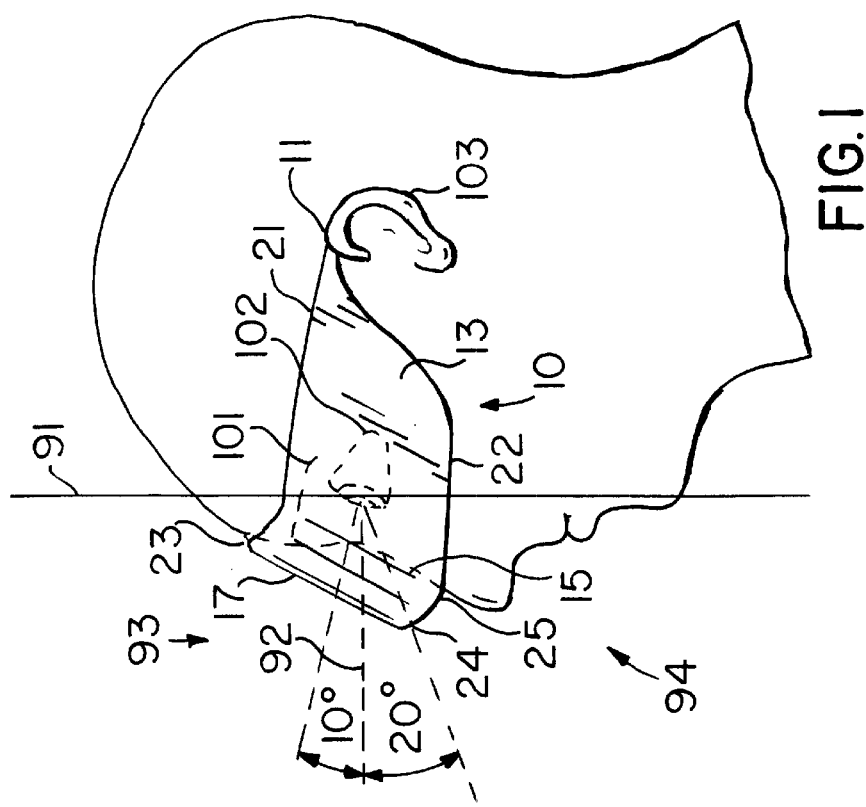
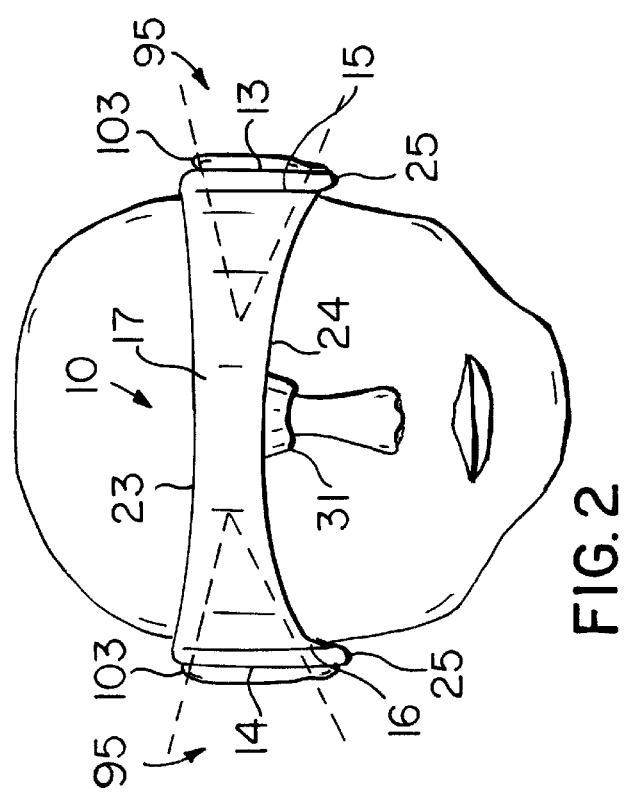

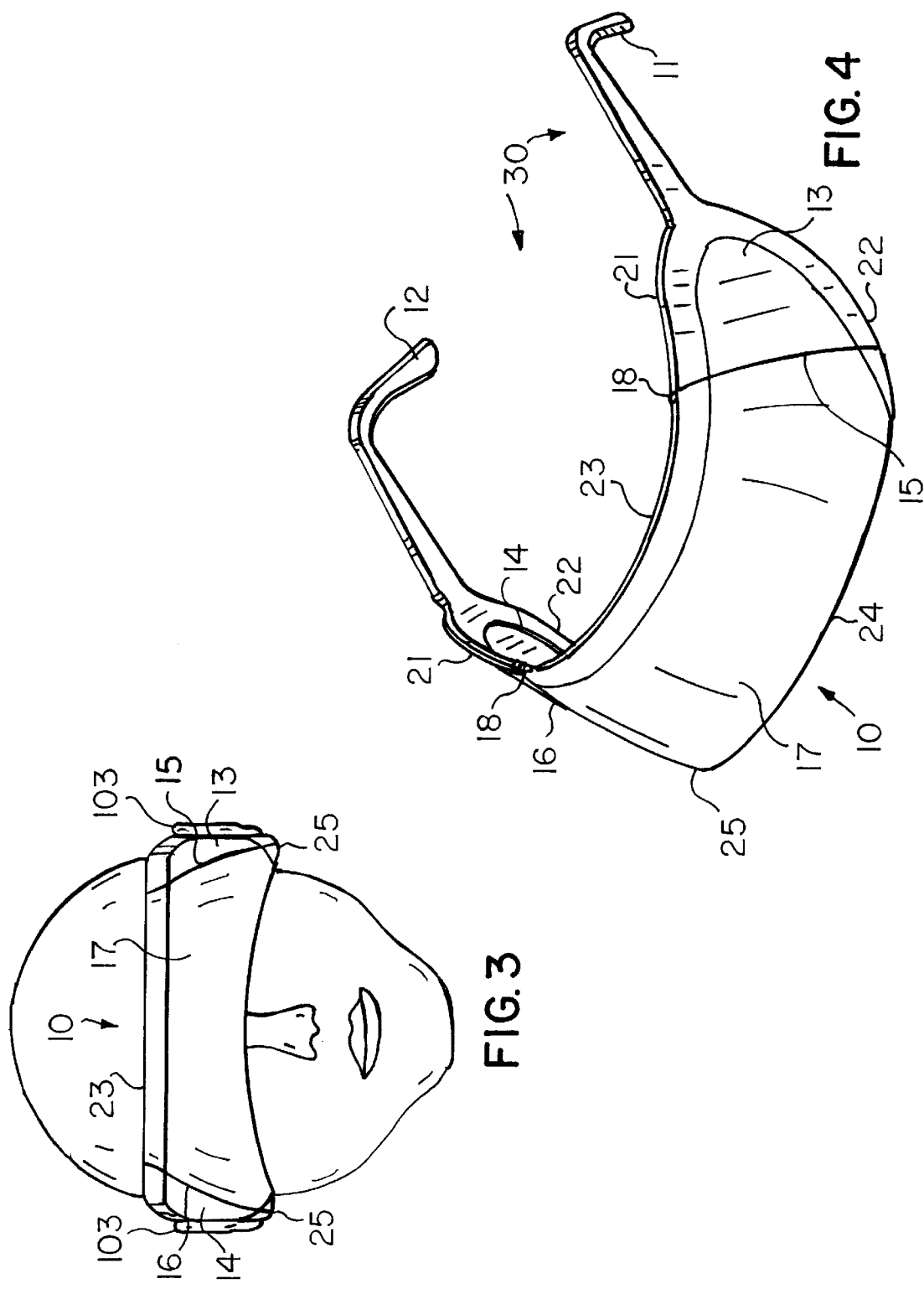

VISION OCCLUDING EYE SHIELD FOR VEHICLE PASSENGERS

BACKGROUND OF THE INVENTION

The invention relates generally to vision occluding devices, such as eye shields or blinders, which are worn on a person's head and are to used to block out or reduce a portion of the normal field of vision. More particularly, the invention relates to such devices which are primarily concerned with occluding peripheral vision. Even more particularly, the invention is related to such devices which also occlude all of the peripheral field of vision and most or all of the superior field of vision while allowing for unobstructed vision over all or most of the inferior field of vision.

Many persons suffer from nausea or queasiness while riding as passengers in a moving vehicle, a condition often referred to as motion or car sickness. Motion sickness is usually intensified when the passenger attempts to read or concentrate on objects within the interior of the vehicle, and it has been estimated that up to 40 percent of passengers who read in a moving vehicle experience some degree of discomfort. Motion sickness is primarily caused by the mixed messages being sent to the brain from the sensory system—the body seems to be at rest yet the inner ear detects some forward motion and objects pass by in the peripheral field of vision. Treatment includes the use of drugs such as Bonine or Dramamine, herbal remedies or acupressure devices, all of dubious efficacy. The typical recommendation is to focus out the front window while turning away from or shielding the vision to the side windows coupled with an admonishment not to read. Researchers theorize that blocking out one of the conflicting sensory messages will greatly reduce the likelihood of motion sickness. Since the actual body motion is restrained due to the confinement of the passenger compartment and since the actual forward motion sensed by the inner ear will be present as long as the vehicle is in motion, it is the visual sensory problem that must be addressed.

Various occluding devices are known, although none of the prior known devices are fully suitable for solving the problem of passenger motion sickness. Some devices are translucent, such as shown in U.S. Pat. No. 4,859,047 to Badewitz, U.S. Pat. No. 4,106,119 to Taupin, U.S. Pat. No. 4,698,022 to Gilson, and U.S. Pat. No. 4,470,673 to Gilson et al., and are mainly directed at reducing glare from incidental or ambient lighting and from the headlights of approaching vehicles, or to simulate varying degrees of visibility in flight training. Other devices are opaque and block out all light transmission and vision through the opaque sections, such as sown in U.S. Pat. No. 3,577,566 to Kislin, U.S. Pat. No. 5,100,224 to Terrasi and U.S. Pat. No. 5,661,534 to Gill—the first two patents having lower edges of specific shape in order to match the configuration of an aircraft instrument panel cowl for training purposes and the latter patent showing an awkward rectilinear configuration having forward telescoping segments to define an elongated tunnel. None of these configurations are suitable for solving the problems of passenger vehicle motion sickness.

It is an object of this invention to provide a vision occluding device or eye shield which solves the visual sensory problem when a passenger is riding in a vehicle, and which is especially useful when the passenger desires to read, write or perform another focused activity in the vehicle, where the device completely occludes the peripheral field of vision such that the wearer is not visually aware of the blurred objects passing through the peripheral field of vision. The device allows the wearer to view objects in the forward field of vision but blocks out all or a significant portion of the superior field of vision above the mid sight line, thereby allowing the wearer to have an unobstructed view of all or most of the inferior field of vision for reading while blocking normal sight lines through the side and forward windows of the vehicle. It is a further object to provide such a device which is physically comfortable for the wearer and which minimizes psychological discomfort or what may be called the blinder effect. These and other objects will be clear from the more detailed disclosure below.

SUMMARY OF THE INVENTION

The invention is in general an eye shield or vision occluding device to be worn by passengers in an automobile or other moving vehicle to block out the field of vision through the side windows and the front window while the wearer is focusing on the interior of the vehicle, and in particular when the wearer is reading a book or magazine, playing portable video games, writing or the like. The eye shield has a means to mount the device on the wearer's head in a secure and stable manner, such as with temple members and a nose bridge to rest the device on the ears and nose of the wearer, or by head straps, means to connect the device to eyeglasses or sunglasses, or incorporation in a hat or the like. The eye shield comprises in general a pair of opaque-to-motion peripheral shield members which block the field of vision to the side and an opaque-to-motion front shield member, angled outwardly downward from the brow line, joined to the peripheral shield members to create a solid occluding device over a lateral range of at least 180 degrees, where the term opaque-to-motion is used to define a condition where passage of light is so restricted that the wearer cannot discern or perceive movement of objects through the shield members. The lower edge of the front shield member is configured to block the major portion of the superior field of vision above the mid sight line, preferably at least approximately the upper 80 degrees, and most preferably to block all of the superior field and at least approximately 20 degrees of the inferior field of vision below the mid sight line, thus defining an unobstructed field of vision suitable for focusing on interior objects yet blocking vision through the windows when the wearer maintains the head in a normal position. The configuration allows the wearer to have limited or no forward vision out the front window with the head maintained in a generally vertical or slightly reclined position, so that the wearer does not to need to remove the device to focus on other objects or to look out of the vehicle by raising or turning the head.

BRIEF DESCRIPTION OF THE DRAWINGS

FIG. 1 is a side view of the invention as worn.

FIG. 2 is a front view of the invention as worn.

FIG. 3 is a front view of an alternative embodiment of the invention as worn.

FIG. 4 is a perspective view of the invention.

DETAILED DESCRIPTION OF THE INVENTION

Figure 5:
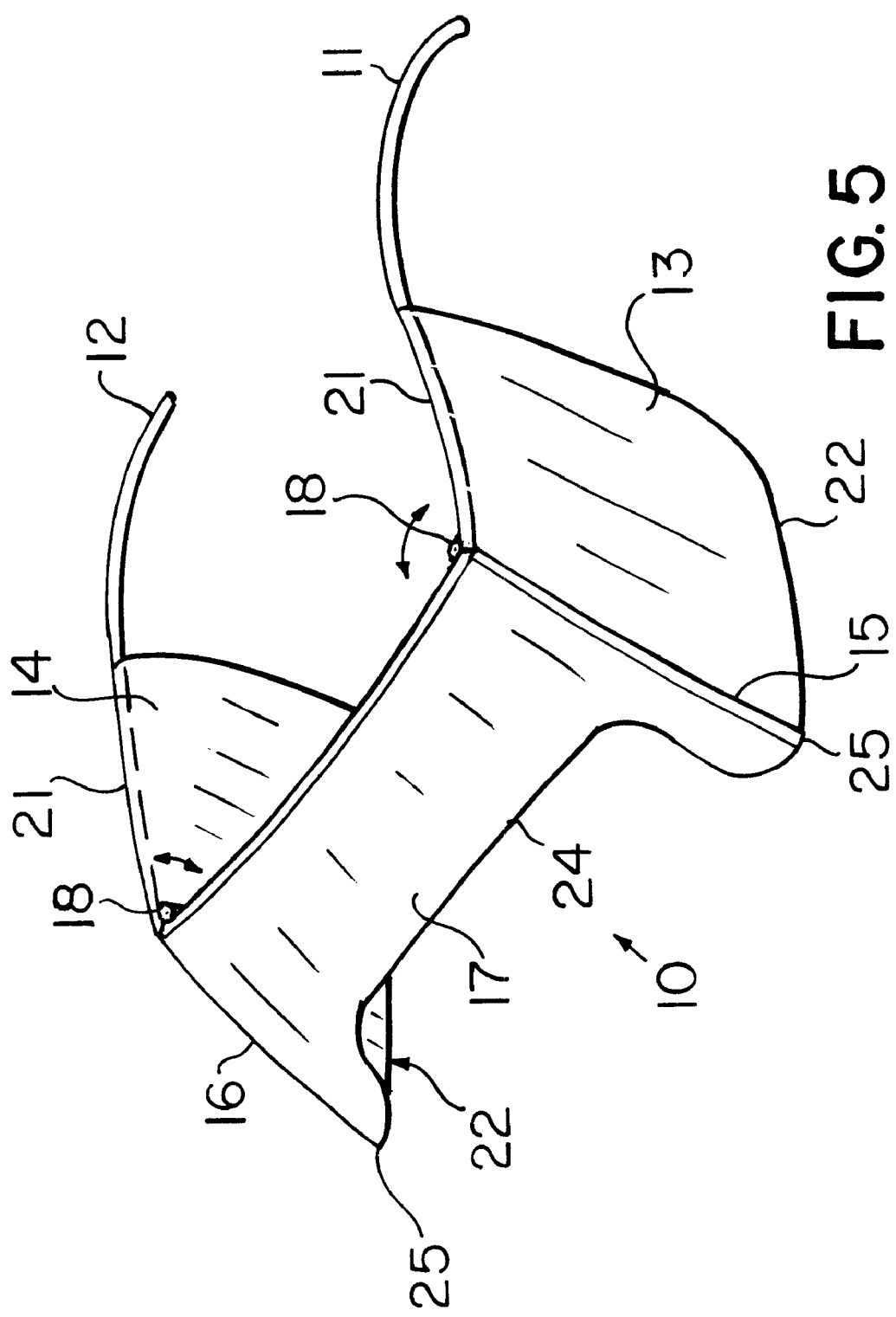
FIG. 5 is a perspective view of a folding embodiment of the invention.

With reference to the drawings, the invention will now be described with regard for the best mode and the preferred embodiment. In general, the invention is a vision occluding device in the nature of an eye shield or blinder which is worn by the passenger in an automobile, especially while reading, to block the line of sight through the front and side windows of the vehicle to prevent queasiness, often referred to as motion sickness, due to the visual input of the scenery outside the vehicle passing by while the user is focusing on the reading material. The eye shield completely blocks the left and right peripheral fields of vision, preferably blocks at least approximately the upper 80 degrees of the superior field of vision, and most preferably blocks an upper portion of the inferior field of vision to the discernment or perception of motion while providing an open, non-occluded area of sight over the lower portion of the inferior field of vision. The eye shield is configured in the general form of eyeglasses or a visor, such that the device is maintained in position on the head by being supported by the ears, pressure against the temples, and/or a nose bridge.

As illustrated in the drawings, the eye shield or vision occluding device 10 comprises in general means 30 for supporting the device on the head of the wearer, which as shown in FIGS. 1 and 2 comprises a left temple member 11 and a right temple member 12 which rest on the ears 103 of the wearer and press against the wearer's temples, a common construction for eyeglasses or visors. The eye shield 10 further comprises a left peripheral shield member 13 and a right peripheral shield member 14, which are joined to or may be formed as a part of the left and right temple members 11 and 12, and a curved forward shield member 17 which is connected to or formed as a single structure with the left and right peripheral shield members 13 and 14 by a left transition portion or juncture 15 and a right transition portion or juncture 16. The eye shield 10 may be constructed so as to be foldable in the common manner of eyeglasses or sunglasses, as shown in FIG. 5, where hinge members 18 of any suitable type join the forward shield member 17 to the peripheral shield members 13 and 14 such that transition junctions 15 and 16 are the conjunction between the forward shield 17 and peripheral shields 13 and 14 when the eye shield 10 is in the open configuration for use. The peripheral shield members 13 and 14 and the forward shield member 17 are opaque-to-motion, which as used herein shall be defined to be the blockage of sufficient light passage through the shield members 13, 14 and 17 to the extent that movement of objects through or across the forward or peripheral field of vision occluded by shield members 13, 14 and 17 is not perceivable or discernable, and are preferably formed of a relatively hard and durable plastic material. The eye shield supporting means 30 may also comprise a nose bridge member 31, or may alternatively comprise an elastic or adjustable strap which encircles the wearer's head, a hat, or clip-on means to connect the eye shield 10 to reading or sunglasses in known manner.

The left and right peripheral shield members 13 and 14 are relatively planar in order to generally match the configuration of the sides of the wearer's head in the temple area. The forward shield member 17 is preferably slightly curved from side to side to better conform to the curvature of the front of the wearer's face. The transition portions 15 and 16 joining the forward shield member 17 to the peripheral shield members 13 and 14 are solid or continuous along the full length of the junctures so that no line of vision passes between the shield members 13 and 17 or 14 and 17. The lower forward shield edge 24 is preferably symmetrically curved with its apex in the middle and its lowermost points at each of the transition lower corners 25, such that the lower peripheral shield edges 22 at least back to the point even with the eye socket lateral edge 102 are always equal to or lower than any point on the lower forward shield edge 24. The curve of the lower forward shield edge 24 may be slight as shown in FIG. 3 or almost U-shaped as shown in FIGS. 2 and 5. The upper forward shield edge 23 is slightly curved to conform to the brow line 101, such that the upper forward shield edge 23 in conjunction with the upper peripheral shield edges 21 which reside adjacent the wearer's temples preclude light passage or line of sight above the eye shield 10 whether the head is positioned in the upright vertical position or tilted forward.

For the eye shield 10 to function as intended to block the field of vision through the side and front windows of a vehicle while allowing the wearer to read and focus on objects below that field of vision, it is necessary that the dimensions and configuration of the eye shield 10 be maintained within specified limits. Vehicle seat backs are typically slightly inclined toward the rear of the vehicle, such that the head and torso of someone occupying the seat will be leaning slightly back from true vertical. For purposes of this disclosure, a mid sight line 92 will be defined as occupying the line of sight when the eyes are neutral in the vertical direction, moved neither up or down, which equates to 90 degrees off the artificial vertical axis 91 taken through the head. Thus with a person standing upright and with the artificial vertical axis 91 head aligned with the true vertical axis, the mid sight line 92 will be horizontal. With the head leaning backward 20 degrees for example, the mid sight line 92 will be 20 degrees above true horizontal. The mid sight line 92 divides the field of view in the vertical direction into two fields, the superior field 93 above the mid sight line 92 and the inferior field 94 below the mid sight line 92. Fields of vision to the left and right side are defined as the peripheral fields 95.

The forward shield member 17 is sized and positioned to block approximately at least the upper 80 degrees of the superior field of vision 93, with a more preferred embodiment blocking all of the superior field and with a most preferred embodiment blocking all of the superior field and an upper portion of the inferior field of vision 94. Defined in another manner, the unoccluded area in the forward field of vision extends no higher than 10 degrees above the mid sight line 92, or more preferably extending no higher than the mid sight line 92, and most preferably extending no higher than 20 degrees below the mid sight line. The peripheral shield members 13 and 14 are sized and positioned to completely block the peripheral field of vision 95. The forward shield member 17 angles outward from the upper forward shield edge 23 along the brow line 101 to the lower forward shield edge 24 in the most preferred embodiment such that a minimum of 20 degrees of the inferior field of vision 94 immediately below the mid sight line 92 is blocked. The height of the forward shield member 17 is determined by the angle of the forward shield member 17 relative to the vertical axis 91. A gently angled forward shield member 17 will be necessarily longer than a steeply angled forward shield member 17 in order to block the upper 20 degrees of the inferior field of vision 94. The upper portion of the inferior field of vision 94 is blocked to account for the angle of the wearer's head when seated in the vehicle, as the mid sight line 92 will be positioned above the true horizontal and thus lower portions of the windows will be visible unless the eye shield 10 extends below the mid sight line 92. It is preferred that the forward shield member 17 be angled at least 25 degrees outward from the vertical axis 91 so that a space is created in front of the user's eyes for both physical and psychological comfort, with a most preferred angle of about 45 degrees in order to maintain the forward extension distance of the lower forward shield edge 24 within a reasonable limit. Alternatively, the forward shield member 17 may be shortened or the angle increased such that less of the inferior field 94 is blocked or a lower portion of the superior field 93 is not blocked, which allows the wearer to have a greater forward field of vision when the head is raised to vertical or tilted back. Since the wearer will normally tilt the head forward or down to read, the eye shield 10 will still function to block the line of vision through the front and side windows of the vehicle. With the forward shield member 17 constructed within the parameters as set forth herein, the eye shield 10 will properly function for individuals of differing heights and in vehicles with differing window configurations.

The peripheral shield members 13 and 14 must extend rearward at least equal to the eye socket lateral edge 102 and preferably extend up to 2 inches beyond. The height of the peripheral shield members 13 and 14 should be between 1.25 and 2.75 inches, with preference given to the larger dimension, such that the lower peripheral shield edges 22 extend at least equal to the bottom of the eye socket and preferably about 0.75 inches below the eye socket and the upper lower peripheral shield edges 21 extend at least equal to and preferably about 0.5 inches above the brow line 101.

It is understood that equivalents and substitutions to certain elements set forth above may be obvious to those skilled in the art, and the true scope and definition of the invention therefor is to be as set forth in the following claims.

I claim:

1. An eye shield device for completely occluding the peripheral field of vision and partially occluding the forward field of vision of the wearer, comprising means for supporting the device on the head of the wearer, a forward shield member which is opaque-to-motion such that the movement of objects is not perceivable therethrough, and peripheral shield members adjoined to said forward shield member which are opaque-to-motion such that the movement of objects is not perceivable therethrough, where said peripheral shield members occlude all of the peripheral field of vision of the wearer and where said forward shield member occludes the upper region of the forward field of vision of the wearer between said peripheral shield members, said forward shield member extending down to between at least 10 degrees above the mid sight line of the wearer and 20 degrees below the mid sight line of the wearer, such that the forward field of vision of the wearer is unoccluded over the range from at least the lower 70 degrees of the inferior field of vision below the mid sight line of the wearer to the lower 10 degrees of the superior field of vision above the mid sight line of the wearer.

2. The device of claim 1, where said forward shield member occludes all of the superior field of vision of the wearer.

3. The device of claim 2, where said forward shield member occludes an upper portion of the inferior field of vision below the mid sight line of the wearer.

4. The device of claim 3, where said forward shield member occludes the upper 20 degrees of the inferior field of vision below the mid sight line of the wearer.

5. The device of claim 1, where said means for supporting are temple members.

6. The device of claim 1, where said peripheral shield members are adjoined to said forward shield member by hinge members such that said device is foldable.

7. The device of claim 1, where each of said peripheral shield members is adapted to extend rearward from said forward shield member at least to the eye socket lateral edge of the wearer, is adapted to extend downward at least to the bottom of the eye socket, and is adapted to extend upward at least to the brow line of the wearer.

8. The device of claim 7, where said forward shield member is adapted to extend upward at least to the brow line of the wearer.

9. The device of claim 1, where said forward shield member is adapted to angle outwardly and downward from the brow line of the wearer.

10. The device of claim 1, where said forward shield member comprises a curved lower edge.

11. The device of claim 10, where said forward shield lower edge is generally U-shaped.

12. An eye shield device for completely occluding the peripheral field of vision and partially occluding the forward field of vision, while simultaneously allowing a portion of the lower field of vision to remain unoccluded, of the passenger in an automobile having side windows and a forward window, comprising means for supporting the device on the head of the wearer, a forward shield member which is opaque-to-motion such that the movement of objects is not perceivable therethrough, and peripheral shield members adjoined to said forward shield member which are opaque-to-motion such that the movement of objects is not perceivable therethrough, where said peripheral shield members occlude all of the peripheral field of vision of the wearer through the side windows of the vehicle and where said forward shield member occludes all of the forward field of vision through the forward window of the vehicle when the head of the wearer is disposed vertically or tilted forward.

13. The device of claim 12, where said means for supporting are temple members.

14. The device of claim 12, where said peripheral shield members are adjoined to said forward shield member by hinge members such that said device is foldable.

15. The device of claim 12, where said forward shield member is adapted to angle outwardly and downward from the brow line of the wearer.

16. The device of claim 12, where said forward shield member comprises a curved lower edge.

17. The device of claim 16, where said forward shield lower edge is generally U-shaped.

18. An eye shield device for completely occluding the peripheral field of vision and partially occluding the upper region of the forward field of vision of the wearer, comprising means for supporting the device on the head of the wearer, a forward shield member which is opaque-to-motion such that the movement of objects is not perceivable therethrough, said forward shield member having a lower edge, and peripheral shield members adjoined to said forward shield member which are opaque-to-motion such that the movement of objects is not perceivable therethrough, where said peripheral shield members occlude all of the peripheral field of vision of the wearer and where said lower edge of said forward shield member is disposed from 10 degrees above the mid sight line of the wearer to 20 degrees below the mid sight line of the wearer, such that the upper region of the forward field of vision of the wearer is occluded over a range between down to 10 degrees above the mid sight line of the wearer to 20 degrees below the mid sight line of the wearer, and further such that the forward field of vision of the wearer is unoccluded over the range from at least the lower 70 degrees of the inferior field of vision below the mid sight line of the wearer to the lower 10 degrees of the superior field of vision above the mid sight line of the wearer.

19. The device of claim 18, where said lower edge of said forward shield member is disposed at the mid sight line of the wearer.

20. The device of claim 18, where said lower edge of said forward shield member is disposed below the mid sight line of the wearer.

* * * * *